United States Patent [19]

Brouwer et al.

[11] Patent Number: 4,979,982
[45] Date of Patent: Dec. 25, 1990

[54] HERBICIDAL CINNAMIC ESTER URACILS

[75] Inventors: Walter G. Brouwer, Guelph; Ethel E. Felauer, Puslinch, both of Canada; Allyn R. Bell, Cheshire, Conn.

[73] Assignees: Uniroyal Chemical Company, Inc., Middlebury, Conn.; Uniroyal Chemical Ltd./Ltee, Don Mills, Canada

[21] Appl. No.: 474,955

[22] Filed: Feb. 2, 1990

[51] Int. Cl.$^5$ .................. A01N 43/54; C07D 239/54
[52] U.S. Cl. ......................................... 71/92; 544/314
[58] Field of Search ............................ 544/314; 71/92

[56] References Cited

U.S. PATENT DOCUMENTS

| | | | |
|---|---|---|---|
| 4,338,318 | 7/1982 | Henrick et al. | 544/314 |
| 4,760,163 | 7/1988 | Wenger et al. | 544/314 |
| 4,859,229 | 8/1989 | Wenper et al. | 544/314 |

OTHER PUBLICATIONS

Plath et al., Chem. Abst. 107-198078a(1987).

Primary Examiner—Cecilia Shen
Attorney, Agent, or Firm—Glenn E. Karta

[57] ABSTRACT

Compounds having the structure

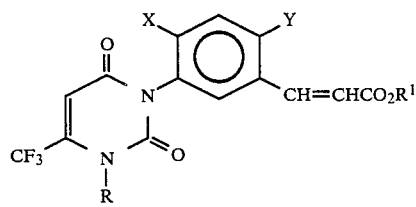

wherein:
R is $C_1$-$C_{12}$ alkyl, linear or branched; or $C_3$-$C_{12}$ alkenyl;
$R^1$ is $C_1$-$C_{12}$ alkyl, linear or branched and can form a carbocycle;
X is hydrogen or halogen; and
Y is hydrogen or halogen;

are disclosed which have herbicidal activity. Herbicidal compositions comprising the compounds and a carrier are also disclosed, as are methods for controlling the growth orf undesirable plants utilizing the compounds. Methods for the preparation of such compounds are also disclosed.

15 Claims, No Drawings

HERBICIDAL CINNAMIC ESTER URACILS

BACKGROUND OF THE INVENTION

1. Field of the Invention

This invention is directed to novel cinnamic ester derivatives of 3-alkyl-4-(trifluoromethyl)uracils which exhibit unexpectedly desirable selective herbicidal activity. In other aspects, this invention is directed to herbicidal compositions comprising such compounds as well as to methods for controlling the growth of plants employing such cinnamic ester derivatives. In yet another aspect, this invention relates to processes for producing such compounds.

Weed control is essential in the cultivation of important agronomic species such as corn, peanuts and cotton, as well as in the cultivation of many horticultural species. Moreover, the presence of such weeds on non-cropped areas may present a fire hazard, or may result in the undesirable drifting of sand or snow or irritation to persons with allergies. Accordingly, control of weeds would be beneficial, particularly in a manner which would allow for the selective control of such plants without concurrent injury to desirable crops or vegetation.

2. Description of Related Art

Chemical Abstracts 107:198078a (1987) relates to certain cinnamic esters, which are said to possess post-emergence herbicidal activity against a series of dicotyledons. However, the cinnamic ester moiety has an isoindole moiety at the 5-position of the benzene ring as opposed to the uracil moiety which is the subject of the compounds of the instant invention.

SUMMARY OF THE INVENTION

In one aspect, this invention relates to a compound of the formula:

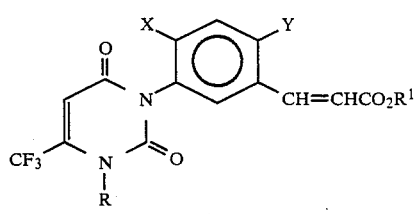

(I)

wherein:

R is $C_1$–$C_{12}$ alkyl, linear or branched; or $C_3$–$C_{12}$ alkenyl;

$R^1$ is $C_1$–$C_{12}$ alkyl, linear or branched and can form a carbocycle;

X is hydrogen or halogen; and

Y is hydrogen or halogen.

In another aspect, this invention relates to a herbicidal composition comprising:

(a) a compound having the structure of formula (I) above as an active ingredient; and (b) a suitable carrier.

In yet another aspect, this invention relates to a method of controlling the growth of undesirable plants, which method comprises applying an herbicidally effective amount of a compound of formula (I) described above.

The present invention is also directed to a method for preparing the compounds of formula (I) as more fully described below.

DETAILED DESCRIPTION OF THE INVENTION

The compounds of formula (I) may be prepared according to the following scheme:

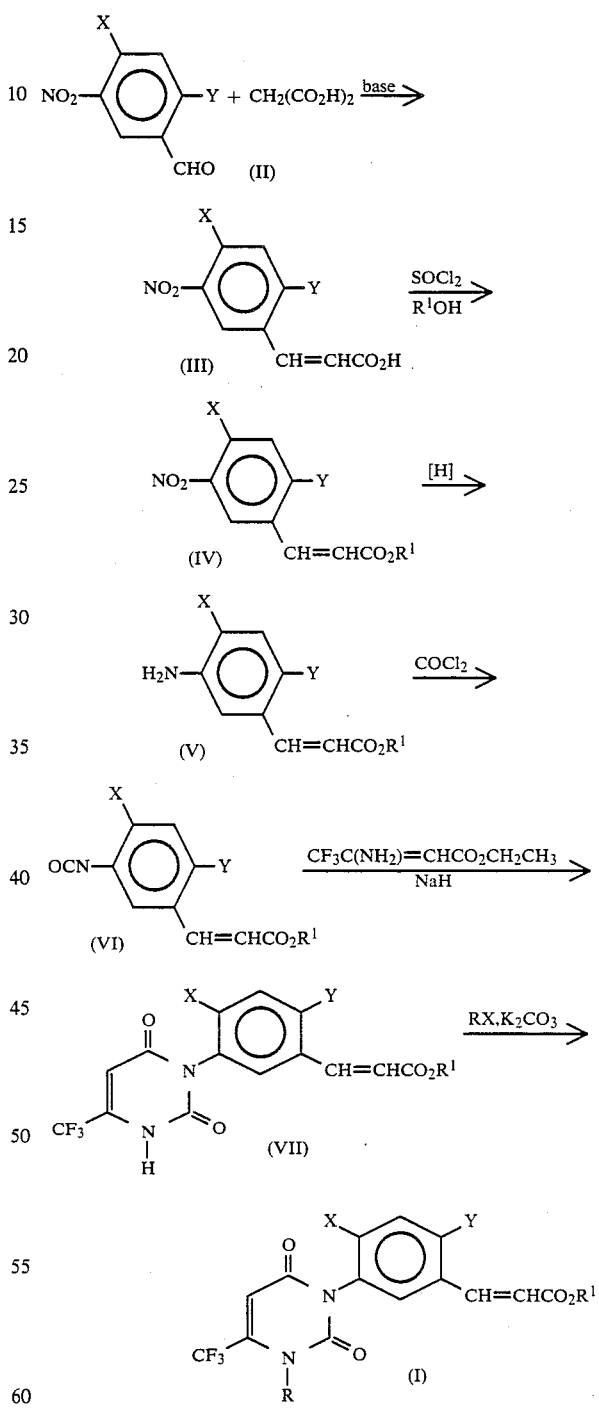

The formation of the cinnamic acid (III) in the first step requires a strong base, e.g., piperidine or morpholine in an organic base solvent, e.g., pyridine. Ester (IV) preparation is accomplished using standard methods known in the art, e.g., by the formation of the acid chloride and subsequent treatment with an appropriate alcohol or by refluxing in excess alcohol with a catalytic amount of mineral acid. Reduction of the nitro (IV) is best done by iron filings in aqueous alcohol with some mineral acid present. The isocyanate (VI) can be made using phosgene gas and ethyl acetate as solvent. The uracil (VII) is made by reacting the isocyanate with the sodium salt of ethyl 3-amino-4,4,4-trifluoro-2-butenoate at sub-zero temperatures. Alkylation of this uracil with an appropriate alkyl halide (RX, where X is halogen) with base, e.g., potassium carbonate in DMF solvent gives the compounds of the invention.

The compositions of this invention are comprised of (a) an herbicidally effective amount of a compound of formula (I) as an active ingredient, and (b) a suitable carrier. Such compositions may comprise one or more of the novel compounds of this invention.

To prepare the compositions, the cinnamic ester uracil may be mixed with an adjuvant to provide compositions in the form of finely-divided particulate solids, granules, pellets, wettable powders, flowable liquids, soluble powders, solutions, and aqueous or organic solvent dispersions or emulsions. Such formulations may be of several different physical and chemical types, and of which could be made by one familiar with the art. For instance, the agriculturally active compound may be impregnated on finely-divided or granular inorganic or organic carriers such as appapulgite clay, sand, vermiculite, corn cob, activated carbon or other granular carriers known to the art. The impregnated granules may then be spread on the soil or incorporated into the soil.

Alternatively, the chemical may be formulated as a wettable powder by grinding it into a fine powder and mixing it with an inactive powdered carrier to which a surface active dispersing agent has been added. Typical Powdered solid carriers are the various mineral silicates (such as mica, talc, pyrophyllite, clays and the like) or Powdered organic materials (e.g., corn cob). The wettable powder may then be dispersed in water and sprayed on the soil surface, or on crop or weed plants.

Similarly, an emulsifiable concentrate may be prepared by dissolving the chemical in a solvent such as naphtha, toluene, or other aromatic or aliphatic hydrocarbon to which a surface active dispersing agent generally has been added. The emulsifiable concentrate may then be dispersed in water and applied by spraying.

The concentration of active chemical in the composition may vary widely typically ranging from about 1% to about 95% by weight. The concentration of active chemical in dispersions applied to the soil or foliage is typically between about 0.002% and about 80% by weight.

Formulations containing the active ingredient(s) may be dispersed in water or an organic liquid (such as oil) and applied to target plants. Surface active agents may be added to the applied solution to increase its qualitative or quantitive range of activity. Suitable surface active agents are well known to those skilled in the art. Reference may be made to McCutcheon's Detergents and Emulsifiers (1980, Allured Publ. Co., Ridgewood, N.J.) for examples of appropriate surface active agents. Similarly, such formulations may be applied to the soil either as a liquid or a granule.

For use as a preemergence herbicide the compounds of this invention are typically applied at a rate of from about 0.01 to about 10 pounds per acre (about 0.01 to about 11 kg/ha) to soil which contains weed and crop seed. Such application is made either to the surface of the soil or into the upper one to three inches (2.5 to 7.5 cm.) of soil. When employed as a postemergence herbicide, the compounds are typically applied at a rate of from about 0.01 to about 10 pounds per acre (about 0.01 to about 11 kg/ha) to the aerial portions of weeds.

The most suitable rate of application in any given case may depend on such factors as soil type, soil pH, soil organic matter content, the quantity and intensity of rainfall before and after treatment, the air and soil temperature, light intensity and light duration per day. All of these factors can have an influence on the efficacy of the chemicals for a given weed control use. However, one skilled in the art can, by routine experimentation, readily determine optimum conditions for employment of any particular compound.

The herbicidal use may include control of vegetation at industrial sites or selective weed control in crop fields.

EXAMPLE

The following Examples are intended to further illustrate the invention and are not intended to limit the scope of the invention in any manner whatsoever.

EXAMPLE 1

Preparation of 1-methylethyl 3-[2-chloro-5-[3,6-dihydro-3-methyl-2,6-dioxo-4-(trifluoromethyl)-1(2H)-pyrimidinyl]phenyl]-2-propenoate (Compound No. 3)

STEP 1:

3-(2-chloro-5-nitrophenyl)-2-propenoic acid

A mixture of 2 chloro-5-nitrobenzaldehyde (100 g., 0.54 mole), malonic acid (122 g., 1.2 mole) in pyridine (300 ml) and piperidine (5 ml) was heated at 100° C. for one hour, during which time considerable gassing occurred. After refluxing the reaction mixture for a further few minutes, it was then cooled. The resulting precipitate was collected, washed with water and dried to give an 80% yield, m.p. 226°–228° C.

STEP 2:

1-methylethyl 3-(2-chloro-5-nitrophenyl)-2-propenoate

The acid from Step 1 (98 g.) was refluxed with thionyl chloride (300 ml) for two hours, after which excess thionyl chloride was removed. To the residue was added isopropyl alcohol (300 ml) and the whole refluxed for 3 hours. On cooling, the product, a yellow precipitate was obtained. After collecting on a filter, the product was washed with aqueous sodium bicarbonate, then water and dried to give an 89% yield, m.p. 74°–75° C.

STEP 3:

1-methylethyl 3-(5-amino-2-chlorophenyl)-2-propenoate

A mixture of ethanol (144 ml), water (41 ml), hydrochloric acid (4.3 ml) and iron powder (63 g. 100 mesh) was stirred and heated to 70° C., whereupon the ester (98 g., 0.36 mole) from Step 2 was added in portions. At each addition, an exotherm developed. After the addition, the reaction mixture was refluxed for three hours before filtering when still hot. On cooling, the product precipitated out. This was collected on a filter, washed with ethanol and dried. A yield of 78%, m.p. 98°–100° C. was obtained.

STEP 4:

1-methylethyl 2-(2-chloro-5-isocyanatophenyl)-2-propenoate

A solution of the ester (26 q) from Step 3 in ethyl acetate (100 ml) was added dropwise to a stirred saturated solution of phosgene in ethyl acetate (200 ml). Stirring was employed and phosgene was continuously bubbled into the solution. After the addition was stopped, distillation of some of the solvent at atmospheric pressure facilitated the removal of excess phosgene and the remainder of the solvent removed on he rotary evaporator. The resulting residue was distilled to give the isocyanate, b.p 133°–140° C. at 0.15 mm, 75% yield.

STEP 5:

1-methylethyl 3-[2-chloro-5-[3,6-dihydro-2,6-dioxo-4-(trifluoromethyl)-1(2H)-pyrimidinyl]phenyl]-2-propenoate, sodium salt Sodium hydride (3.4 g.. 60%, 0.88 mole) was washed with ligroin, covered with dry THF (200 ml) and at 0° C. with stirring treated with ethyl 3-amino-4-trifluoro-2-butenoate (14.6 g, 0.08 mole) in dry THF (100 ml) added dropwise over 30 minutes. The mixture was cooled to −70° C. using dry ice/acetone bath and treated with a solution of the isocyanate (21.6 g, 0.08 mole) in dry THF (100 ml) over ten minutes. After the addition, the reaction was stirred at −70° C. for two hours before allowing to come to ambient temperatures and left overnight. Most of the THF was removed and sufficient methylene chloride was added to Precipitate the sodium salt of the uracil. The sodium salt was collected on a filter washed with methylene chloride, then ligroin (b.p. 30°–60° C.) and dried, 94% yield.

STEP 6:

1-methylethyl 3-[2-chloro-5-[3,5-dihydro-3-methyl-2,6-dioxo-4-(trifluoromethyl)-1(2H)-pyrimidinyl]-phenyl]-2-propenoate Sodium salt (8.4 g, 0.02 mole) from Step 5, in DMF (25 ml) was treated with methyl iodide (3 ml) and stirred at ambient temperature overnight. Water was added and the resulting Precipitate was collected on a filter and recrystallized from isopropyl alcohol to give the product, m.p. 200°–202° C., whose NMR and IR was consistent with the structure (I), X=H, Y=Cl, R=$CH_3$, $R^1$=$CH(CH_3)_2$.

EXAMPLE 2

Preparation of 1-methylethyl 3-[2-chloro-4-fluoro-5-[3,6-dihydro-2,6-dioxo-3-methyl-4-(trifluoromethyl)-1(2H)-pyrimidinyl]-phenyl]-2-propenoate (Compound No. 5)

STEP 1:

3-(2-chloro-4-fluorophenyl)-2-propenoic acid

As in Example 1, Step 1, the product was a white solid m.p. 253°–255° C. obtained in 75% yield.

STEP 2:

3-(2-chloro-4-fluoro-5-nitrophenyl)-2-propenoic acid

The product of Step 1 (51 g. 0.25 mole) was dissolved in concentrated sulfuric acid (250 ml) and cooled to −5° C. Fuming nitric acid (14 ml, d 1.5) was added dropwise at less than 0° C. The nitrating mixture was allowed to come to ambient temperature and left overnight. A white precipitate was obtained when the reaction was poured onto ice (3 kg), collected on a filter, washed with water and dried, m.p. 164°–171° C., yield 80%.

STEP 3:

1-methylethyl 3-(2-chloro-4-fluoro-5-nitrophenyl)-2-propenoate

As in Example 1, Step 2, the product was isolated in 66% yield, m.p. 95°–96° C.

STEP 4:

1-methylethyl 3-(5-amino-2-chloro-4-fluorophenyl)-2-propenoate

As in Example 1, Step 3, the product was prepared in 76% yield with m.p. 72°–75° C.

STEP 5:

1-methylethyl 3-(2-chloro-4-fluoro-5-isocyanatophenyl-2-propenoate

As in Example 1, Step 4, the product was obtained in 54% yield with b.p. 135°–143° C. at 0.3 mm.

STEP 6:

1-methylethyl 3-[2-chloro-4-fluoro-5-[3,6-dihydro-2,6-dioxo-3methyl-4-(triflouromethyl)-1(2H)-pyrimidinyl]-phenyl]-2-propenoate, sodium salt In a manner similar to Example 1, Step 5, this sodium salt was isolated.

STEP 7:

1-methylethyl 3-[2-chloro-4-fluoro-5-[3,6-dihydro-2,6-dioxo-3-methyl-4-(trifluoromethyl)-1(2H)-pyrimidinyl]phenyl]-2-propenoate The sodium salt (6.0 g, 0.014 mole) from Step 6 in isopropyl alcohol (25 ml) and dimethylsulfate (18 g. 0.015 mole) were mixed and the reaction mixture was stirred and heated for two hours at 80° C., then left at ambient temperature overnight. After removing inorganic material by filtration, followed by evaporation of the solvent, a yellow precipitate was obtained in 33% yield with m.p. 137°–139° C.

NMR, and IR spectra, as well as elemental analysis of the final products and intermediates, were consistent with theoretical values.

EXAMPLE 3

Additional compounds within the scope of this invention were prepared using essentially the procedures outlined above. The structures and melting points of these compounds are summarized in Table I below.

TABLE I

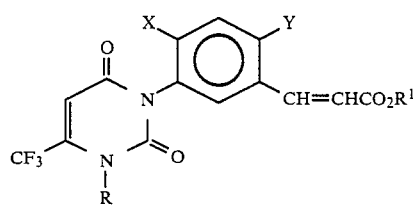

| Compound | R | X | Y | $R^1$ | M.P. °C. |
|---|---|---|---|---|---|
| 1 | H | H | Cl | $CH(CH_3)_2$ | 260–264 |
| 2 | Na | H | Cl | $CH(CH_3)_2$ | 300 |
| 3 | $CH_3$ | H | Cl | $CH(CH_3)_2$ | 205–207 |
| 4 | $CH_2CHCH_2$ | H | Cl | $CH(CH_3)_2$ | 134–136 |
| 5 | $CH_3$ | F | Cl | $CH(CH_3)_2$ | 137–139 |
| 6 | $CH_3$ | F | Cl | $CH(CH_3)CH_2CH_3$ | 131–133 |
| 7 | $CH_3$ | F | Cl | $CH(CH_2CH_3)_2$ | 106–107 |
| 8 | $CH_3$ | H | H | $CH(CH_3)_2$ | 128–130 |

EXAMPLE 4

Preemergence Control

To illustrate the effectiveness of the novel compounds of this invention as preemergence herbicides, 300 mg of each of the below listed compounds were dissolved in 10 ml acetone to which 30 mg of an emulsifying agent, ethoxylated sorbitan monlaurate, were added. The solution was diluted to 100 ml with distilled water. Ten milliliters of the 3000 ppm solution were diluted to 250 ppm with distilled water. The chemical was applied at the rate of 10 lb/A (11.2 kg/ha) by drenching 46 ml of the 250 ppm solution on the surface of soil in 4½ inch (11.25 cm) plastic pots wherein seeds of the following weeds had been planted: velvet leaf (*Abutilon theophrasti* Medic.) (VL), jimsonweed (*Datura stramonium* L.) (JW), tall morningglory (*Ipomea purpurea* L. Roth) (TM), switchgrass (*Panicum viroatum* L.) (SG), barnyard grass (*Echinclchloa crus-galli* (L.) Beauv.) (BG), green foxtail (*Setaria viridis*) (L.) Beauv.) (GF). The percent control of the weeds compared to untreated checks was determined two weeks after treatment. The results of such testing are summarized in Table II. The data presented in such table indicates the good to excellent herbicidal efficacy exhibited by the compounds of this invention.

TABLE II

Preemergence Activity
(% Control at 11.2 kg/ha)

| Compound | VL | JW | TM | BG | SG | GF |
|---|---|---|---|---|---|---|
| 1 | 50 | 50 | 0 | 0 | 0 | 0 |
| 2 | 95 | 0 | 0 | 0 | 0 | 0 |
| 3 | 100 | 100 | 100 | 100 | 100 | 100 |
| 4 | 25 | 40 | 0 | 70 | 75 | 100 |
| 5 | 100 | 100 | 100 | 100 | 100 | 100 |
| 6 | 100 | 100 | 100 | 100 | 100 | 100 |
| 7 | 100 | 100 | 25 | 100 | 100 | 100 |
| 8 | 0 | — | 0 | 0 | 0 | 0 |

EXAMPLE 5

Postemergence Control

To test the effectiveness of the compounds of this invention as postemergence herbicides, a 3000 ppm solution (produced in accordance with the process described under Example 4) was atomized employing a DEVILBISS [trademark] sprayer, wetting the foliage to the drip point. The remainder of the procedure was the same as described under Example 4. The weeds, which were the same species as described under Example 4, were treated six days after emergence. The percent weed control was evaluated two weeks after treatment. The results of such testing are summarized in Table III.

TABLE III

Postemergence Activity
(% Control at 3000 ppm)

| Compound | VL | JW | TM | BG | SG | GF |
|---|---|---|---|---|---|---|
| 1 | 0 | 5 | 0 | 10 | 0 | 10 |
| 2 | 0 | 0 | 5 | 0 | 0 | 0 |
| 3 | 100 | 100 | 100 | 100 | 100 | 100 |
| 4 | 50 | 40 | 35 | 25 | 5 | 35 |
| 5 | 100 | 100 | 100 | 100 | 100 | 100 |
| 6 | 100 | 100 | 100 | 100 | 100 | 100 |
| 7 | 100 | 100 | 100 | 100 | 100 | 100 |
| 8 | 95 | 10 | 90 | 100 | 25 | 60 |

TABLE III-continued

Postemergence Activity
(% Control at 3000 ppm)

The above data demonstrate the desirable selective postemergent herbicidal control exhibited by the compounds of the present invention.

We claim:

1. A compound of the formula:

wherein:
R is $C_1$-$C_{12}$ alkyl, linear or branched; $C_3$-$C_{12}$ alkenyl;
$R^1$ is $C_1$-$C_{12}$ alkyl, linear or branched and can form a carbocycle;
X is hydrogen or halogen; and
Y is hydrogen or halogen.

2. The compound of claim 1 wherein R is methyl; X is hydrogen; Y is chlorine and $R^1$ is $CH(CH_3)_2$.

3. The compound of claim 1 wherein R is methyl; X is fluorine; Y is chlorine and $R^1$ is $CH(CH_3)_2$.

4. The compound of claim 1 wherein R is methyl; X is fluorine; Y is chlorine and $R^1$ is $CH(CH_3)CH_2CH_3$.

5. The compound of claim 1 wherein R is methyl; X is fluorine; Y is chlorine and $R^1$ is $CH(CH_2CH_3)_2$.

6. An herbicidal composition comprising (A) an herbicidally effective amount of a compound according to claim 1, and (B) a suitable carrier.

7. The composition of claim 6 wherein R is methyl; X is hydrogen; Y is chlorine and $R^1$ is $CH(CH_3)_2$.

8. The composition of claim 6 wherein R is methyl; X is fluorine; Y is chlorine and $R^1$ is $CH(CH_3)_2$.

9. The composition of claim 6 wherein R is methyl; X is fluorine; Y is chlorine and $R^1$ is $CH(CH_3)CH_2CH_3$.

10. The composition of claim 6 wherein R is methyl; X is fluorine; Y is chlorine and $R^1$ is $CH(CH_2CH_3)_2$.

11. A method for controlling the growth of undesirable plants comprising applying to the locus of such plants an herbicidally effective amount of a compound in accordance with claim 1.

12. The method of claim 11 wherein R is methyl; X is hydrogen; Y is chlorine and $R^1$ is $CH(CH_3)_2$.

13. The method of claim 11 wherein R is methyl; X is fluorine; Y is chlorine and $R^1$ is $CH(CH_3)_2$.

14. The method of claim 11 wherein R is methyl; X is fluorine; Y is chlorine and $R^1$ is $CH(CH_3)CH_2CH_3$.

15. The method of claim 11 wherein R is methyl; X is fluorine; Y is chlorine and $R^1$ is $CH(CH_2CH_3)_2$.

* * * * *